United States Patent [19]
Elliott et al.

[11] Patent Number: 6,051,599
[45] Date of Patent: Apr. 18, 2000

[54] ENDOTHELIN RECEPTOR ANTAGONISTS

[75] Inventors: John Duncan Elliott, Wayne; Aiming Gao, Chester Springs, both of Pa.

[73] Assignee: SmithKline Beecham Corporation, Philadelphia, Pa.

[21] Appl. No.: 09/399,434

[22] Filed: Sep. 20, 1999

Related U.S. Application Data

[62] Division of application No. 08/737,851, filed as application No. PCT/US96/12583, Aug. 2, 1996
[60] Provisional application No. 60/010,983, Feb. 1, 1996, and provisional application No. 60/001,793, Aug. 2, 1995.
[51] Int. Cl.$^7$ ........................ A61K 31/381; C07D 409/02
[52] U.S. Cl. .............................................. 514/444; 549/60
[58] Field of Search .................................. 549/60; 514/444

[56] References Cited

U.S. PATENT DOCUMENTS

| | | |
|---|---|---|
| 4,402,971 | 9/1983 | Edwards . |
| 5,691,373 | 11/1997 | Berryman et al. . |
| 5,719,182 | 2/1998 | Cousins et al. . |

*Primary Examiner*—Robert W. Ramsuer
*Attorney, Agent, or Firm*—Linda E. Hall; Stephen A. Venetianer; Charles M. Kinzig

[57] ABSTRACT

Novel furans and thiophenes, pharmaceutical compositions containing these compounds and their use as endothelin receptor antagonist are described.

14 Claims, No Drawings

ENDOTHELIN RECEPTOR ANTAGONISTS

This is a divisional of application Ser. No. 08/737,851 filed Feb. 2, 1998; which is a 371 of international Application No. PCT/US96/12583, filed Aug. 2, 1996; which claims the benefit of the following provisional applications: 60/001,793, filed Aug. 2, 1995 and 60/010,983, filed Feb. 1, 1996

FIELD OF INVENTION

The present invention relates to furans and thiophenes pharmaceutical compositions containing these compounds and their use as endothelin receptor antagonists.

Endothelin (ET) is a highly potent vasoconstrictor peptide synthesized and released by the vascular endothelium. Endothelin exists as three isoforms, ET-1, ET-2 and ET-3. [Unless otherwise stated "endothelin" shall mean any or all of the isoforms of endothelin]. Endothelin has profound effects on the cardiovascular system, and in particular, the coronary, renal and cerebral circulation. Elevated or abnormal release of endothelin is associated with smooth muscle contraction which is involved in the pathogenesis of cardiovascular, cerebrovascular, respiratory and renal pathophysiology. Elevated levels of endothelin have been reported in plasma from patients with essential hypertension, acute myocardial infarction, subarachnoid hemorrhage, atherosclerosis, and patients with uraemia undergoing dialysis.

In vivo, endothelin has pronounced effects on blood pressure and cardiac output. An intravenous bolus injection of ET (0.1 to 3 nmol/kg) in rats causes a transient, dose-related depressor response (lasting 0.5 to 2 minutes) followed by a sustained, dose-dependent rise in arterial blood pressure which can remain elevated for 2 to 3 hours following dosing. Doses above 3 nmol/kg in a rat often prove fatal.

Endothelin appears to produce a preferential effect in the renal vascular bed. It produces a marked, long-lasting decrease in renal blood flow, accompanied by a significant decrease in GFR, urine volume, urinary sodium and potassium excretion. Endothelin produces a sustained antinatriuretic effect, despite significant elevations in atrial natriuretic peptide. Endothelin also stimulates plasma renin activity. These findings suggest that ET is involved in the regulation of renal function and is involved in a variety of renal disorders including acute renal failure, cyclosporine nephrotoxicity, radio contrast induced renal failure and chronic renal failure.

Studies have shown that in vivo, the cerebral vasculature is highly sensitive to both the vasodilator and vasoconstrictor effects of endothelin. Therefore, ET may be an important mediator of cerebral vasospasm, a frequent and often fatal consequence of subarachnoid hemorrhage.

ET also exhibits direct central nervous system effects such as severe apnea and ischemic lesions which suggests that ET may contribute to the development of cerebral infarcts and neuronal death.

ET has also been implicated in myocardial ischemia (Nichols et al. Br. J. Pharm. 99:597–601, 1989 and Clozel and Clozel, Circ. Res., 65: 1193–1200, 1989) coronary vasospasm (Fukuda et al., Eur. J. Pharm. 165: 301–304, 1989 and Luscher, Circ. 83: 701, 1991) heart failure, proliferation of vascular smooth muscle cells, (Takagi, Biochem & Biophys. Res. Commun.; 168: 537–543, 1990, Bobek et al., Am. J. Physiol. 258:408-C415, 1990) and atherosclerosis, (Nakaki et al., Biochem. & Biophvs. Res. Commun. 158: 880–881, 1989, and Lerman et al., New Eng. J. of Med. 325: 997–1001, 1991). Increased levels of endothelin have been shown after coronary balloon angioplasty (Kadel et al., No. 2491 Circ. 82: 627, 1990).

Further, endothelin has been found to be a potent constrictor of isolated mammalian airway tissue including human bronchus (Uchida et al., Eur J. of Pharm. 154: 227–228 1988, LaGente, Clin. Exp. Allergy 20: 343–348, 1990; and Springall et al., Lancet, 337: 697–701, 1991). Endothelin may play a role in the pathogenesis of interstitial pulmonary fibrosis and associated pulmonary hypertension, Glard et al., Third International Conference on Endothelin, 1993, p. 34 and ARDS (Adult Respiratory Distress Syndrome), Sanai et al., Supra, p. 112.

Endothelin has been associated with the induction of hemorrhagic and necrotic damrage in the gastric mucosa (Whittle et al., Br. J. Pharm. 95: 1011–1013, 1988); Raynaud's phenomenon, Cinniniello et al., Lancet 337: 114–115, 1991); Crohn's Disease and ulcerative colitis, Munch et al., Lancet, Vol. 339, p. 381; Migraine (Edmeads, Headache, Feb. 1991 p 127); Sepsis (Weitzberg et al., Circ. Shock 33: 222–227, 1991; Pittet et al., Ann. Surg. 213: 262–264, 1991), Cyclosporin-induced renal failure or hypertension (Eur. J. Pharmacol., 180: 191–192, 1990, Kidnev Int, 37: 1487–1491, 1990) and endotoxin shock and other endotoxin induced diseases (Biochem, Biophvs. Res. Commun., 161: 1220–1227, 1989, Acta Physiol. Scand. 137: 317–318, 1989) and inflam-matory skin diseases. (Clin Res. 41:451 and 484, 1993).

Endothelin has also been implicated in preclampsia of pregnancy. Clark et al., Am. J. Obstet. Gvnecol. March 1992, p. 962–968; Kamor et al., N. Eng. J. of Med., Nov 22, 1990, p. 1486–1487; Dekker et al., Eur J. Ob. and Gyn. and Rep. Bio. 40 (1991) 215–220; Schiff et al., Am. J. Ostet. Gvnecol. Feb 1992, p. 624–628; diabetes mellitus, Takahashi et al., Diabetologia (1990) 33:306–310; and acute vascular rejection following kidney transplant, Watschinger et al., Transplantation Vol. 52. No. 4, pp. 743–746.

Endothelin stimulates both bone resorption and anabolism and may have a role in the coupling of bone remodeling. Tatrai et al. Endocrinology, Vol. 131, p. 603–607.

Endothelin has been reported to stimulate the transport of sperm in the uterine cavity, Casey et al., J. Clin. Endo and Metabolism, Vol. 74, No. 1, p. 223–225, therefore endothelin antagonists may be useful as male contraceptives. Endothelin modulates the ovarian/menstrual cycle, Kenegsberg, J. of Clin. Endo. and Met., Vol. 74, No. 1, p. 12, and may also play a role in the regulation of penile vascular tone in man, Lau et al., Asia Pacific J. of Pharm., 1991, 6:287–292 and Tejada et al., J. Amer. Phvsio. Soc. 1991, H1078–H1085. Endothelin also mediates a potent contraction of human prostatic smooth muscle, Langenstroer et al., J. Urology, Vol. 149, p. 495–499.

Thus. endothelin receptor antagonists would offer a unique approach toward the pharmacotherapy of hypertension, acute and chronic renal failure, ischemia induced renal failure, sepsis-endotoxin induced renal failure, prophylaxis and/or treatment of radio-contrast induced renal failure, acute and chronic cyclosporin induced renal failure, cerebrovascular disease, stroke, subarachnoid hemorrhage, cerebrovascular spasm, myocardial ischemia, angina, congestive heart failure, acute coronary syndrome, myocardial salvage, unstable angina, asthma, primary pulmonary hypertension, pulmonary hypertension secondary to intrinsic pulmonary disease. atherosclerosis, Raynaud's phenomenon, ulcers, sepsis, migraine, glaucoma, endotoxin shock, endotoxin induced multiple organ failure or disseminated intravascular coagulation, cyclosporin-induced renal failure and as an adjunct in angioplasty for prevention of restenosis, diabetes, diabetic retinopathy, retinopathy, diabetic nephropathy, diabetic macrovascular disease, atherosclerosis, preclampsia of pregnancy, bone remodeling, kidney transplant, male contraceptives, infertility and priapism and benign prostatic hypertrophy.

SUMMARY OF THE INVENTION

This invention comprises compounds represented by Formula (I) and pharmaceutical compositions containing these compounds, and their use as endothelin receptor antagonists which are useful in the treatment of a variety of cardiovascular and renal diseases including but not limited to: hypertension, acute and chronic renal failure, cyclosporine induced nephrotoxicity, benign prostatic hypertrophy, pulmonary hypertension, migraine, stroke, subarachnoid hemorrhage, cerebrovascular vasospasm, myocardial ischemia, angina, congestive heart failure, atherosclerosis, diabetic nephropathy, diabetic retinopathy, retinopathy, diabetic macrovascular disease, atherosclerosis and as an adjunct in angioplasty for prevention of restenosis.

This invention further constitutes a method for antagonizing endothelin receptors in an animal, including humans, which comprises administering to an animal in need thereof an effective amount of a compound of Formula (I).

In a further aspect the present invention provides a process for the preparation of a compound of Formula (I).

DETAILED DESCRIPTION OF THE INVENTION

The compounds of this invention are represented by structural Formula (I):

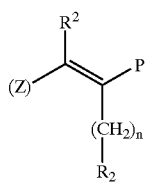

(I)

wherein Z is

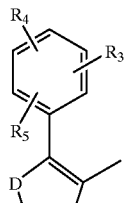 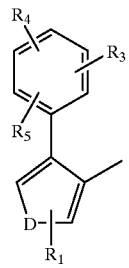 or 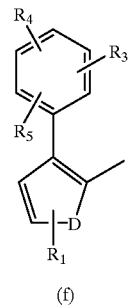

(d) (e) (f)

D is O or S;
P is tetrazol-5-yl, $CO_2R_6$ or $C(O)N(R_6)S(O)_qR_{10}$;
$R^a$ is independently hydrogen or $C_{1-6}$alkyl;
$R_1$ is independently hydrogen, Ar, $C_{1-6}$alkyl or $C_{1-6}$alkoxy;

$R_2$ is Ar, $C_{1-8}$alkyl, $C(O)R_{14}$ or

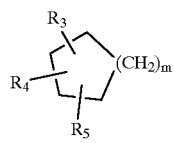

(c)

$R_3$ and $R_5$ are independently $R_{13}OH$, $C_{1-8}$alkoxy, $S(O)_qR_{11}$, $N(R_6)_2$, $NO_2$, Br, F, I, Cl, $CF_3$, $NHCOR_6$, $R_{13}CO_2R_7$, $-X-R_9-Y$, $-X(C(R_6)_2)OR_6$, $-(CH_2)_mX'R_8$ or $-X(CH_2)_nR_8$ wherein each methylene group within $-X(CH_2)_nR_8$ may be unsubstituted or substituted by one or two $-(CH_2)_nAr$ groups;

$R_4$ is independently $R_{11}$, OH, $C_{1-5}$alkoxy, $S(O)_qR_{11}$, $N(R_6)_2$, Br, F, I, Cl or $NHCOR_6$, wherein the $C_{1-5}$alkoxy may be unsubstituted or substituted by OH, methoxy or halogen;

$R_6$ is independently hydrogen or $C_{1-8}$alkyl;

$R_7$ is independently hydrogen, $C_{1-10}$alkyl, $C_{2-10}$alkenyl or $C_{2-8}$alkynyl, all of which may be unsubstituted or substituted by one or more OH, $N(R_6)_2$, $CO_2R_{12}$, halogen or $XC_{1-10}$alkyl; or $R_7$ is $(CH_2)_nAr$;

$R_8$ is independently $R_{11}$, $CO_2R_7$, $CO_2C(R_{11})_2O(CO)XR_7$, $PO_3(R_7)_2$, $SO_2NR_7R_{11}$, $NR_7SO_2R_{11}$, $CONR_7SO_2R_{11}$, $SO_3R_7$, $SO_2R_7$, $P(O)(OR_7)R_7$, CN, $CO_2(CH_2)_mC(O)N(R_6)_2$, $C(R_{11})_2N(R_7)_2$, $C(O)N(R_6)_2$, $NR_7C(O)NR_7SO_2R_{11}$, $OR_6$, or tetrazole which is substituted or unsubstituted by $C_{1-6}$alkyl;

$R_9$ is independently a bond, $C_{1-10}$alkylene, $C_{1-10}$alkenylene, $C_{1-10}$alkylidene, $C_{1-10}$alkynylene, all of which may be linear or branched, or phenylene, all of which may be unsubstituted or substituted by one of more OH, $N(R_6)_2$, COOH or halogen;

$R_{10}$ is independently $C_{1-10}$alkyl, $N(R_6)_2$ or Ar;

$R_{11}$ is independently hydrogen, Ar, $C_{1-8}$alkyl, $C_{2-8}$alkenyl, $C_{2-8}$alkynyl, all of which may be unsubstituted or substituted by one or more OH, $CH_2OH$, $N(R_6)_2$ or halogen;

$R_{12}$ is independently hydrogen, $C_{1-6}$alkyl, $C_{2-6}$alkenyl or $C_{2-7}$alkynyl;

$R_{13}$ is independently divalent Ar, $C_{1-10}$alkylene, $C_{1-10}$alkylidene, $C_{2-10}$alkenylene, all of which may be unsubstituted or substituted by one or more OH, $CH_2OH$, $N(R_6)_2$ or halogen;

$R_{14}$ is independently hydrogen, $C_{1-10}$alkyl, $XC_{1-10}$alkyl, Ar or XAr;

$R_{15}$ is independently $C_{1-6}$alkyl or phenyl substituted by one or two $C_{1-6}$alkyl, OH, $C_{1-5}$alkoxy, $S(O)_qR_6$, $N(R_6)_2$, Br, F, L, C, $CF_3$ or $NHCOR_6$;

X is independently $(CH2)_n$, O, $NR_6$ or $S(O)_q$;

X' is independently O, $NR_6$ or $S(O)_q$;

Y is independently $CH_3$ or $X(CH_2)_nAr$;

Ar is:

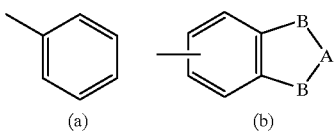

(a)     (b)

naphthyl, indolyl, pyridyl, thienyl, oxazolidinyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $Z_1$ or $Z_2$ groups;

A is independently C=O, or $(C(R_6)_2)_m$;

B is independently —$CH_2$— or —O—;

$Z_1$ and $Z_2$ are independently hydrogen, $XR_6$, $C_{1-8}$alkyl, $(CH_2)_qCO_2R_6$, $C(O)N(R_6)_2$, CN. $(CH_2)_nOH$, $NO_2$, F, Cl, Br, I, $N(R_6)_2$, $NHC(O)R_6$, $O(CH_2)_mC(O)NR_aSO_2R_{15}$, $(CH_2)_mOC(O)NR_aSO_2R_{15}$, $O(CH_2)_mNR_aC(O)NR_aSO_2R_{15}$ or tetrazolyl which may be substituted or unsubstituted by $C_{1-6}$alkyl, $CF_3$ or $C(O)R_6$;

m is independently 1 to 3;

n is independently 0 to 6;

q is independently 0, 1 or 2;

provided $R_3$, $R_4$ and $R_5$ are not O—$O(CH_2)_n$Ar or O—$OR_6$;

or a pharmaceutically acceptable salt thereof.

All alkyl, alkenyl, alkynyl and alkoxy groups may be straight or branched.

Halogen may be Br, Cl, F or I.

The compounds of the present invention may contain one or more asymmrnetric carbon atoms and may exist in racemic and optically active form. All of these compounds and diastereoisomers are contemplated to be within the scope of the present invention. Preferred compounds are those wherein:

P is $CO_2R_6$; more preferably P is $CO_2H$.

$R_1$ is hydrogen.

$R_2$ is Ar, cyclohexyl or $C_{1-4}$alkyl. More preferably $R_2$ is a group Ar wherein Ar is a group (a) or (b). In said group (a) or (b) $Z_1$ and $Z_2$ are independently hydrogen, $CO_2R_6$, $(CH_2)_nOH$, $C_{1-4}$alkyl or $C_{1-6}$alkoxy, e.g. methoxy; A is preferably $CH_2$, and one or both Bs are preferably O.

$R_3$ and $R_5$ are independently hydrogen, $CO_2R_6$, OH, $C_{1-8}$alkoxy, $C_{1-8}$alkyl. $N(R_6)_2$, $NO_2$, Br, F, Cl, I, $R_{13}CO_2R_7$, $X(CH_2)_nR_8$, $(CH_2)_mX'R_8$, or $X(C(R_6)_2)_mOR_6$;

In the context of the group $R_3$ and $R_5$ preferably do not represent hydrogen. In particular in the group $R_3$ preferably represents Br, Cl, $C_{1-8}$alkoxy e.g. methoxy; $X(CH_2)_nR_8$, wherein X preferably represents O, n is 0,1, or 2, and $R_8$ is preferably selected from:

$CO_2R_6$ wherein $R_6$ is preferably hydrogen;

$OR_6$ wherein $R_6$ is preferably H;

tetrazolyl optionally substituted by $C_{1-8}$alkyl e.g. ethyl;

$CONR_7SO_2R_{11}$ wherein $R_7$ is H or $C_{1-8}$alkyl e.g. methyl, $R_{11}$ preferably is $C_{1-8}$alkyl (e.g. methyl, isopryl, or t-butyl) or phenyl optionally substituted by Br, Cl, F, $C_{1-8}$alkyl e.g. methyl;

or $R_8$ is phenyl or pyridyl substituted by one or more Br, Cl, $CO_2H$, $CH_2OH$.

$R_5$ is $C_{1-8}$alkoxy e.g. methoxy, or $N(R_6)_2$ wherein $R_6$ preferably is H or methyl.

$R_4$ is hydrogen, OH, $C_{1-5}$alkoxy, $N(R_6)_2$, Br, F, Cl, I, $NHCOCH_3$, or $S(O)_q$ $C_{1-5}$alkyl wherein the $C_{1-5}$alkyl may be unsubstituted or substituted by OH, methoxy or halogen. R4 is more preferably hydrogen;

$R_6$ is hydrogen or $C_{1-8}$alkyl e.g. methyl and ethyl;

$R_7$ is hydrogen, $C_{1-10}$alkyl, $C_{2-10}$alkenyl or $C_{2-8}$alkynyl, all of which may be unsubstituted or substituted by one or more OH, $N(R_6)_2$, $CO_2R_{12}$, halogen, or $R_7$ is $(CH_2)_n$Ar. When $R_7$ is $(CH_2)_n$Ar, n is preferably zero or 1 and Ar is preferably phenyl substituted or unsubstituted by halogen or $C_{1-5}$alkoxy.

$R_{11}$ is hydrogen, phenyl, pyridyl wherein the phenyl and pyridyl may be substituted or unsubstituted by one or two $C_{1-4}$alkyl groups; $C_{1-8}$alkyl, $C_{2-8}$alkenyl, $C_{2-8}$alkynyl, all of which may be substituted or unsubstituted by one or more OH, $CH_2OH$, $N(R_6)_2$, or halogen;

$R_{12}$ is hydrogen or $C_{1-6}$alkyl.

$R_{13}$ is phenyl, pyridyl, or $C_{2-10}$alkylene, all of which may be unsubstituted or substituted by one or more $CO_2R_6$, OH, $CH_2OH$, $N(R_6)_2$, or halogen;

$R_{15}$ is preferably hydrogen or $C_{1-6}$alkyl e.g. ethyl, isopropyl, n-butyl, cyclopropylmethyl or cyclopropylethyl.

The preferred compounds are:

E-3-[3-[2-(2-carboxyphenyl)methoxy4-methoxy]phenylfur-2-yl]-2-[2-methoxy-4,5-methylenedioxyphenyl]methyl-prop-2-enoic acid, E-3-[3-[2-(2-carboxyphenyl)methoxy4-methoxy]phenylthien-2-yl]-2-[2-methoxy4,5-methylenedioxy]methyl-prop-2-enoic acid and E-3-[4-[2-(2-carboxyphenyl)methoxy-4-methoxy]phenylfur-3-yl]-2-    [2-methoxy-4,5-methylenedioxyphenyl]methyl-prop-2-enoic acid.

The present invention provides compounds of Formula (I).

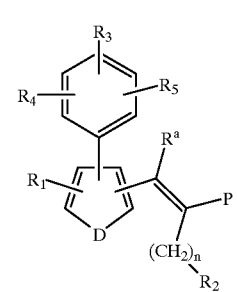

(I)

which can be prepared by a process which comprises:

treating an aryl halide of Formula (2)

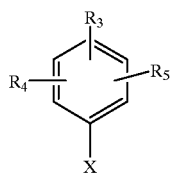
(2)

with an appropriate alkyllithium reagent such as n-butyllithium in tetrahydrofuran followed by addition of a borate such as truisopropyl borate and acidic work up affords a boronic acid of Formula (3)

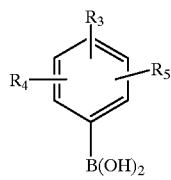
(3)

Reaction of a boronic acid of Formula (3) with a compound of Formula (4)

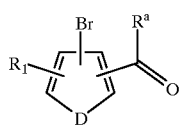
(4)

in the presence of a suitable base such as potassium carbonate with a palladium catalyst such as tetrakis(triphenylphosphine)palladium(0) in a mixture of toluene, ethanol and water at approximately 80–100° C. provides a compound of Formula of

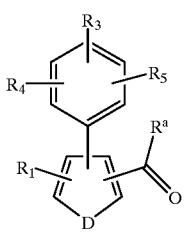
(II)

A compound of Formula (4) may be prepared from a dibromide of Formula (6) by

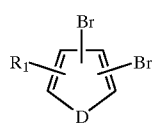
(6)

monohalogen-metal exchange using an appropriate alkyl-lithium reagent such as n-Butyllithium in tetrahydrofuran followed by addition of an alkylating agent (eg. N,N-dimethylformate or $R^aCOCl$).

Knoevenagel condensation of an aldehyde of Formula (II) with a half acid of Formula (7)

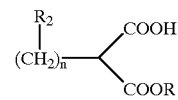
(7)

in a solvent such as benzene at reflux, in the presence of piperidinium acetate with azeotropic removal of water using a Dean-Stark apparatus, affords an ester of Formula (8)

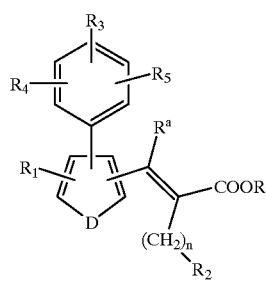
(8)

Saponification of an ester of Formula (8) using aqueous sodium hydroxide in a solvent such as ethanol provides, after acidification with aqueous hydrochloric acid, an acid of Formula (1), wherein P=COOH.

The invention also is a process for preparing compounds of Formula (I) by:
(a) Reaction of a compound of Formula (II)

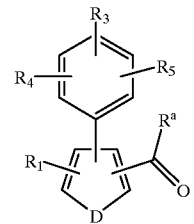
(II)

or a protected form or precursor thereof (as defined hereinafter) with a compound of Formula (7)

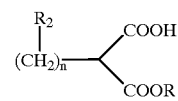
(7)

(wherein $R_2$ is defined for Formula (I) hereinabove); followed if necessary or desired by:
(b) conversion of one compound of Formula (I) into a different compound of Formula (I) e.g.
  (i) when Formula (I) contains a group $CO_2R_6$, $CO_2R_7$ or $CO_2R_{12}$ wherein $R_6$, $R_7$ or $R_{12}$ is alkyl, conversion to a corresponding compound where $R_6$, $R_7$ or $R_{12}$ represents hydrogen;
  (ii) when Formula (I) contains a hydroxy group (e.g. in $R_3$, $R_4$ or $R_5$) conversion to a different group, e.g. a group $(CH_2)Ar$ where Ar is optionally substituted phenyl, by method well known in the art; and/or (c) salt formation.

It will be appreciated by those skilled in the art that the substitutents $R_3$, $R_4$, $R_5$; and $Z_1$ and $Z_2$ may be introduced at any appropriate stage of the synthesis, preferably at an early stage, using methods well known in the art. In some of the reactions depicted above, particularly those in the early stages of the overall synthesis, one or more of the substitutents may therefore represent a precursor for the eventual substituent. A precursor for any of the substitutents means a group which may be derivatised or converted into the desired group. It will be further appreciated that it may be necessary or desirable to protect certain of these substitutents(or their precursors) at various stages in the reaction sequence. Suitable precursors and protecting groups are well known to those skilled in the art, as are methods for their conversion or removal respectively.

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavouring or colouring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the invention are administered in accordance with the present invention.

The biological activity of the compounds of Formula (I) are demonstrated by the following tests:

I. Binding Assay

A) CHO cell membrane preparation.

CHO cells stably transfected with human $ET_A$ and $ET_B$ receptors were grown in 245 mm ×245 mm tissue culture plates in Dulbecco's modified Eagle's medium supplemented with 10% fetal bovine serum. The confluent cells were washed with Dulbecco's phosphate-buffered saline containing a protease inhibitor cocktail (5 mM EDTA, 0.5 mM PMSF, 5 ug/ml of leupeptin and 0.1 U/ml of aprotinin) and scraped in the same buffer. After centrifugation at 800 ×g, the cells were lysed by freezing in liquid nitrogen and thawing on ice followed by homogenization (30 times using a glass dounce homogenizer) in lysis buffer containing 20 mM Tris HCl, pH 7.5, and the protease inhibitor cocktail. After an initial centrifugation at 800 ×g for 10 min to remove unbroken cells and nuclei, the supernatants were centrifuged at 40,000 ×g for 15 min and the pellet was resuspended in 50 mM Tris HCl, pH 7.5, and 10 MM $MgCl_2$ and stored in small aliquots at −70° C. after freezing in liquid $N_2$. Protein was determined by using the BCA method and BSA as the standard.

(B) Binding studies.

[$^{125}$I]ET-1 binding to membranes prepared from CHO cells was performed following the procedure of Elshourbagy et al. (1993). Briefly, the assay was initiated in a 100 ul volume by adding 25 ul of [$^{125}$I]ET-1 (0.2–0.3 nM) in 0.05% BSA to membranes in the absence (total binding) or presence (nonspecific binding) of 100 nM unlabeled ET-1. The concentrations of membrane proteins were 0.5 and 0.05 ug per assay tube for $ET_A$ and $ET_B$ receptors, respectively. The incubations (30° C., 60 min) were stopped by dilution with cold buffer (20 mM Tris HCl, pH 7.6, and 10 mM $MgCl_2$) and filtering through Whatman GF/C filters (Clifton, N.J.) presoaked in 0.1% BSA. The filters were washed 3 times (5 ml each time) with the same buffer by using a Brandel cell harvester and were counted by using a gamma counter at 75% efficiency.

The following examples are illustrative and are not limiting of the compounds of this invention.

EXAMPLE 1

(E)-4-n-Butyl-3-[[2-(2-carboxylphenyl)methoxy-4-methoxylphenyl]thiophen-2-yl]-2-[(2-methoxy-4,5-methylenedioxyphenyl)methyl]-prop-2-enoic acid a) 3-Bromo-4-butylthiophene To a stirred solution of 3,4-dibromothiophene (4.60 g, 20.90 mmol) in dry Et$_2$O (50 mL) at −78° C. was dropwise added n-BuLi (2.5 M, 16.72 mL, 41.80 mmol) under Ar. After stirring for 15 min, a solution of freshly distilled di-n-butyl sulfate in dry Et$_2$O (10 mL) was dropwise added through an addition funnel. The mixture was allowed to warm to room temperature and stirred overnight. 30 mL of 12 M NH$_4$OH was added to the mixture. After stirring for 1 h, the mixture was partitioned between H$_2$O and Et$_2$O. The organic layer was separated and washed with H$_2$O, brine and dried (MgSO$_4$). Removal of the solvent under reduced pressure afforded the title compound as an oil (2.50 g, 60%).

b) 3-Bromo4-n-butylthiophene-2-carboxaldehyde

To a solution of freshly prepared LDA (11.40 mmol) in THF (7 mL) at −78° C. was added slowly 3-bromo-4-butylthiophene of Example 1(a) (2.50 g, 11.40 mmol) in THF (10 mL). After stirring for 15 min, DMF (0.94 mL, 12.10 mmol) in THF (2 mL) was dropwise added. The resulting mixture was stirred for 1 h at −78° C. and then allowed to warm to room temperature. The reaction was quenched with water and extracted with EtOAc (2×50 mL). The combined organic extracts were washed with H$_2$O, brine and dried (MgSO$_4$). After removing the solvent under reduced pressure, column chromatography (silica gel, EtOAc/Hexane, 20:80) of the residue afforded the title compound as an oil (1.87 g, 60%).

c) 4-n-Butyl-3-(2-methoxymethoxy-4-methoxyphenyl)thiophene-2-carboxaldehyde

To a solution of 3-Bromo-4-n-butylthiophene-2-carboxaldehyde of Example 1(b) 1.87 g, 7.57 imuol) in toluene (35 mL) was added (PPh$_3$)$_4$Pd (0.30 g, 0.20 mmol), Na$_2$CO$_3$ (2 M, 9 ML), EtOH (25 mL) and (2-methoxymethoxy-4-methoxyphenyl)boronic acid (1.76 g, 8.30 mmol), respectively. The resulting mixture was stirred at reflux for 3 h. After quenching with water and extraction with EtOAc, the organic extract was washed with H$_2$O, brine and dried (MgSO$_4$). The solvent was removed under reduced pressure and column chromatography (silica gel, EtOAc/Hexane, 25:75) of the residue afforded the title compound as an oil (1.80 g, 71%)

d) Ethyl (E)-3-[4-n-butyl-3-(2-methoxymethoxy4-methoxy)phenylthiophen-2-yl]-2-[(2-methoxy-4,5-methylenedioxy)phenylmethyl]-2-propenoate 4-n-Butyl-3-(2-methoxymethoxy-4-methoxyphenyl)thiophene-2-carboxaldehyde of Example 1(c) (1.05 g, 3.15 mmol), diethyl 2-(2-methoxy-4,5-methylenedioxybenzyl)-malonate (1.25 g, 4.12 mmol), piperidine (0.10 mL, 1.1 mmol) and AcOH (0.11 mL, 1.80 mmol) were dissolved in benzene (30 mL) and refluxed with azetropic removal of water overnight. The solvent was removed under reduced pressure and column chromatography (silica gel, EtOAc/Hexane, 30:70) of the residue afforded the title compound as an oil (0.80 g, 45%).

e) Ethyl (E)-3-[4-n-butyl-3-(2-hydroxy-4-methoxy)phenylthiophen-2-yl]-2-[(2-methoxy-4,5-methylenedioxy)phenylmethyl]-2-propenoate To a solution of Ethyl (E)-3-[4-n-butyl-3-(2-methoxymethoxy-4-methoxyphenyl)-thiophen-2-yl]-2-[(2-methoxy-4,5-methylenedioxy)phenylmethyl]-1-2-propenoate of Example 1(d) (0.80 g, 1.41 mmol) in MeOH (20 mL) was added 0.5 mL of conc. HCl. The mixture was refluxed for 2 h, and then the solvent was removed under reduced pressure. The residue was partitioned between H$_2$O and EtOAc. and the organic layer was separated and washed with H$_2$O, brine and dried (MgSO$_4$). After removing the solvent, column chromatography (silica gel, EtOAc/Hexane, 30:70) of the residue gave the title compound as an oil (0.65 g; 87%).

f) Ethyl (E)-3-[4-n-butyl-3-[2-(2-methoxycarbonyl)phenylmethoxy-4-methoxyphenyl)]-tophen-2-yl]-2-[(2-methoxy-4,5-methylenedioxy)phenylmethyl]-2-propenoate To a solution of Ethyl (E)-3-[4-n-butyl-3-(2-hydroxy-4-methoxy)phenylthiophen-3-yl]-2-[(2-methoxy4,5-methylenedioxy)phenylmethyl]-2-propenoate of Example 1(e) (0.65 g, 12.30 mmol) in DMF (5 mL) was added the prewashed NaH (0.64 g, 16.00 mmol) at 0° C. After stirring for 10 min methyl 2-(bromomethyl) benzoate (0.32 g, 14.70 mrnol) was added. The resulting mixture was stirred for 2 h at room temperature and then partitioned between EtOAc and 5% HCl. The organic layer was separated, washed with H$_2$O, brine and dried (MgSO$_4$). After removing the solvent under reduced pressure column chromatography (silica gel, EtOAC/Hexane, 30:70) of the residue to afforded the title compound as an oil (0.65 g, 78%).

g) (E) 3-[4-n-Butyl-3-[2-(2-carboxyphenyl)methoxy-4-methoxy]phenylthiophen-2-yl]-2-[(2-methoxy-4,5-methylenedioxy)phenylmethyl]-prop-2-enoic acid To a solution of the ester of Example 1(f) (0.65 g, 0.96 mmol) in EtOH (30 mL) was added 1 mL of aqueous NaOH (0.19 g, 4.80 mmol) and the mixture was heated at reflux for 2 h. The reaction was quenched with 5% HCl and the resulting mixture was extracted with EtOAc (3×30 mL). The combined organic extracts were washed with H$_2$O, brine and dried (MgSO$_4$). After removing the solvent under reduced pressure, the resulting residue was crystallized upon standing. Recrystallization from EtOAc/Hexane (1:2) gave the title compound as white solid (0.28g, 46%): mp 165–167° C. $^1$H NMR (400 MHz ,DMSO-d$_6$) δ 0.70 (t, J=7.20 Hz, 3H), 1.08–1.15 (m,2H), 1.29–1.37 (m,2H), 2.28–2.35(m, 2H), 3.28–3.40(br.,2H), 3.80 (s, 6H), 5.40–5.49 (m, 2H) 5.88 ( s, 2H), 6.29 (s, 1H), 6.61 (d, J=2.3 Hz, 1H), 6.70 (dd. J=2.3, 8.4 Hz, 1H), 6.80 (s, 1H), 7.09 (d, J=8.4 Hz), 7.26 (br. d, 1H), 7.35–7.42 (m, 2H), 7.43 (s, 1H), 7.71 (s, 1H), 7.93 (br.d, 1H) Anal. Calcd for C$_{35}$H$_{34}$SO$_9$: C,66.65; H, 5.43. Found: C 66.31; H, 5.54.

EXAMPLE 2

(E)-3-[3-[(2-Carboxyphenyl)methoxy-4-methoxy]phenylthiophen-2-yl]-2-[(2-methoxy-4,5-methlenedioxyphenyl)methyl]-prop-2-enoic acid a) 3-(2-Methoxymethoxy-4-methoxyphenyl)thiophene-2-carboxaldehyde Following the procedure of Example 1(c), but substituting 3-Bromo-4-n-butylthiophene-2-carboxaldehyde with 3-bromothiophene, the title compound was prepared in 89% yield.

b) Ethyl (E)-3-[3-(2-methoxymethoxy-4-methoxy)phenylthiophen-2-yl]-2-[(2-methoxy-4,5-methylenedioxy)phenylmethyl]-2-propenoate Following the procedure of Example 1 (d), but subsituting 4-n-Butyl-3-(2-methoxymethoxy-4-methoxyphenyl)thiophene-2-carboxaldehyde with 3-(2-methoxymethoxy-4-methoxy)phenylthiophene-2-carboxaldehyde, the title compound was prepared in 33% yield.

c) Ethyl (E)-3-[3-(2-hydroxy-4-methoxy)phenylthiophen-2-yl]-2-[(2-methoxy-4,5-methylenedioxy)phenylmethyl]-2-propenoate Following the procedure of Example 1(e), but subsitituting Ethyl (E)-3-[4-n-butyl-3-(2-methoxymethoxy4-methoxy)phenylthiophen-2-yl]-2-[(2-methoxy-4,5-methylenedioxy)phenylmethyl]-2-propenoate with Ethyl (E)-3-[3-(2-methoxymethoxy-4-methoxy)phenylthiophen-2-yl]-2-[(2-methoxy-4,5-methylenedioxy)phenylmethyl]-2-propenoate, the title compound was prepared in 41% yield.

d) Ethyl (E)-3-[3-(2-methoxycarbonylphenyl4-methoxy)phenylthiophen-2-yl]-2-[(2-methoxy-4,5-methylenedioxy)phenylmethyl]-2-propenoate Following the procedure of Example of 1(f), but subsitituting Ethyl (E)-3-[4-n-butyl-3-(2-hydroxy-4-methoxy) phenylthiophen-3-yl]-2-[(2-methoxy-4,5-methylenedioxy) phenylmethyl]-2-propenoate with Ethyl (E)-3-[3-(2-hydroxy-4-methoxy)phenylthiophen-2-yl]-2- [(2-methoxy4,5-methylenedioxy)phenylmethyl]-2-propenoate, the title compound was prepared in 75% yield.

e) (E)-3-[3- [2-(2-Carboxyphenyl)methoxy-4-methoxy] phenylthiophen-2-yl]-2-[(2-methoxy-4,5-methlenedioxy) phenylmethyl]- prop-2-enoic acid Following the procedure of Example 1(g), but subsitituting-Ethyl (E)-3-[4-n-butyl-3-[2-(2-methoxycarbonyl)phenylmethoxy-4-methoxy] phenylthiophen-2-yl]-2-[(2-methoxy-4,5-methylenedioxy) phenylmethyl]-2-propenoate with Ethyl (E)-3-[3-[2-(2-methoxycarbonyl)phenylmethoxy-4-methoxy] phenylthiophen-2-yi]-2-[(2-methoxy-4,5-methylenedioxy) phenylmethyl]-2-propenoate, the title compound was prepared as a white solid in 60% yield. mp 228–231° C. (400 MHZ ,CDCl$_3$) δ 3.70 (s,2H), 3.82 (s,3H), 3.84 (s,3H), 5.56 (s, 2H), 6.45 (s, 1H), 6.53 (s, 1H), 6.63 (dd, J=2.0, 8.30 Hz, 1H), 6.72 (d, J=1.8 Hz, 1H), 7.14 (d, J=5.0 Hz, 1H), 7.21 (d, J=8.5 Hz, 1H), 7.33–7.43 (m, 1H), 7.43 (d, J=5.0 Hz, 1H), 7.49 (s, 1H), 7.49 (d, J=3.5 Hz, 1H), 8.0 (s, 1H), 8.08 (d, J=7.5 Hz, 1H).Anal. Calcd for $C_{31}H_{26}SO_9 \cdot 0.25H_2O$:C, 64.30; H,4.61. Found: C, 64.20; H, 4.65.

EXAMPLE 3

(E)-3-[3-[2-(2-Carboxyphenyl)methoxy-4-methoxy] phenylfuran-2-yl]-2-[(2-methoxy-4,5-methylenedioxy)phenylmethyl]-prop-2-enoic acid a) 3-Bromofuran-2-carboxaldehyde To a solution of freshly prepared LDA (6.80 mmol) in THF (4 mL) at −78° C. was added slowly 3-bromofuran (1.00 g, 6.80 mmol) in THF (5 mL). After stirring for 15 min, DMF (0.56 mL, 7.20 mmol) in THF (2 mL) was dropwise added. The resulting mixture was stirred for 1 h at −78° C. and then allowed to warm to room temperature. The reaction was quenched with water and extracted with EtOAc (2×50 mL). The combined organic extracts were washed with H$_2$O, brine and dried (MgSO$_4$). After removing the solvent under reduced pressure, column chromatography (silica gel, EtOAc/Hexane, 20:80) of the residue afforded the title compound as an oil (0.49 g, 41%).

b) 3-(2-Methoxymethoxy-4-methoxy)phenylfuran-2-carboxaldehyde

To a solution of 3-bromofuran-2-carboxaldehyde of Example 3(a) (0.40 g, 1.29 mmol) in toluene (25 mL) was added (PPh$_3$)$_4$Pd (0.09 g, 0.06 mmol), Na$_2$CO$_3$ (2 M, 3 mL), EtOH (7 mL) and 2-methoxymethoxy-4-methoxyphenylboronic acid (0.29 g, 2.75 mmol), respectively. The resulting mixture was stirred at reflux for 2 h. After quenching with water and extraction with EtOAc, the organic extract was washed with H$_2$O, brine and dried (MgSO$_4$). The solvent was removed under reduced pressure and column chromatography (silica gel, EtOAc/Hexane, 25:75) of the residue afforded the title compound as an oil (0.60 g, 100%)

c) Ethyl (E)-3-[3-(2-methoxymethoxy-4-methoxy) phenylfuran-2-yl]-2-[(2-methoxy-4,5-methylenedioxy) phenylmethyl]-2-propenoate 3-(2-Methoxymethoxy-4-methoxy)phenylfuran-2-carboxaldehyde of Example 3(b) (0.62 g, 2.37 mmol), diethyl 2-(2-methoxy-4,5-methylenedioxybenzyl)-malonate (0.93 g, 3.10 mmol), piperidine (0.10 mL, 1.10 mmol) and AcOH (0.07 mL, 1.20 mmol) were dissolved in benzene (30 mL) and refluxed with azetropic removal of water overnight. The solvent was removed under reduced pressure and column chromatography (silica gel, EtOAc/Hexane, 30:70) of the residue afforded the title compound as an oil (0.42 g, 36%).

d) Ethyl (E)-3-[3-(2-hydroxy-4-methoxy)phenylfuran-2-yl]-2- [(2-methoxy-4,5-methylenedioxy)phenylmethyl]-2-propenoate Ethyl (E)-3-[3-(2-methoxymethoxy-4-methoxy) phenylfuran-2-yl]-2-[(2-methoxy-4,5-methvlenedioxy) phenylmethyl]-2-propenoate of Example 3(c) (0.43 g, 0.85 mmol) in MeOH (20 nL) was added 0.5 mL of conc. HCl. The mixture was refluxed for 2 h, and then the solvent was removed under reduced pressure. The residue was partitioned between H$_2$O and EtOAc. The organic layer was separated and washed with H$_2$O, brine and dried (MgSO$_4$). After removing the solvent, column chromatography (silica gel, EtOAc/Hexane, 30:70) of the residue gave the title compound as an oil (0.16 g, 41%).

e) Ethyl (E)-3-[3-(2-methoxycarbonyl)phenylmethoxy-4-methoxy)phenylfuran-2-yl]-2-[(2-methoxy-4,5-methylenedioxy)phenylmethyl]-2-propenoate To a solution of Ethyl (E)-3-[3-(2-hydroxy -4-methoxy) phenylfuran-2-yl]-2-[(2-methoxy-4,5-methylenedioxy) phenylmethyl]-2-propenoate of Example 3(d) (0.16 g, 0.35 mmol) in DMF (5 mL) was added the prewashed NaH (0.02 g, 0.53 mmol) at 0° C. After stirring for 10 nin methyl 2-(bromomethyl) benzoate (0.09 g, 0.42 mmol) was added. The resulting mixture was stirred for 2 h at room temperature and then partitioned between EtOAc and 5% HCl. The organic layer was separated, washed with H$_2$O. brine and dried (MgSO$_4$). After removing the solvent under reduced pressure, columni chromatography (silica gel, EtOAC/Hexane, 30:70) of the residue afforded the title compound as an oil (0.25 g, 97%).

f) (E)-3-[3-[2-(2-Carboxyphenyl)methoxy4-methoxy] phenylfuran-2-yl]-2-[(2-methoxy-4,5-methylenedioxy) phenylmethyl]-2-propenoic acid To a solution of the ester of Example 3(e) (0.21 g, 0.34 mmol) in EtOH (20 mL) was added 1 mL of aqueous NaOH ( 0.07 g, 1.70 mmol) and the mixture was heated at reflux for 2 h. The reaction was quenched with 5% HCl and the resulting mixture was extracted with EtOAc (3×30 mL). The combined organic extracts were washed with H$_2$O. brine and dried (MgSO$_4$). After removing the solvent under reduced pressure, the resulting residue was crystallized upon standing. Recrystallization from EtOAcJHexane (1:2) gave the title compound as white solid (0.09 g, 47%): mp 212–215 OC. $^1$H NMR (400 MHz ,DMSO-d$_6$) δ 3.73 (s, 3H), 3.81 (s, 3H), 3.93 (s, 2H), 5.47 (s, 2H) 5.89 (s, 2H), 6.40 (s, 1H), 6.69–6.75 (m, 2H), 6.27 (s, 2H), 7.21 9d, J=2.0 Hz, 1H), 7.42–7.45 (m, 1H), 7.46 (s, IH), 7.53–7.58 (m, 2H), 7.81 (d, J=1.71 Hz, 1H), 7.93 (d, J=7.8 Hz, 1H). Anal. Calcd for $C_{31}H_{26}O_{10} \cdot 0.25H_2O$:C, 66.13; H,4.74. Found: C, 66.12; H, 4.73.

EXAMPLE 4

Formulations for pharmaceutical use incorporating compounds of the present invention can be prepared in various forms and with numerous excipients. Examples of such formulations are given below.

Inhalant Formulation

A compound of Formula I, (1 mg to 100 mg) is aerosolized from a metered dose inhaler to deliver the desired amount of drug per use.

| Tablets/Ingredients | Per Tablet |
|---|---|
| 1. Active ingredient (Cpd of Form. I) | 40 mg |
| 2. Corn Starch | 20 mg |
| 3. Alginic acid | 20 mg |
| 4. Sodium Alginate | 20 mg |
| 5. Mg stearate | 1.3 mg |
|  | 2.3 mg |

Procedure for Tablets:

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its conversion to wet granules.

Step 3 The wet mass is converted to granules by passing it through an oscillating granulator using a No. 8 mesh (2.38 mm) screen.

Step 4 The wet granules are then dried in an oven at 140° F. (60° C.) until dry.

Step 5 The dry granules are lubricated with ingredient No. 5.

Step 6 The lubricated granules are compressed on a suitable tablet press.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then steriled by filtration through a 0.22 micron membrane filter and sealed in sterile containers.

We claim:

1. A compound of Formula (I):

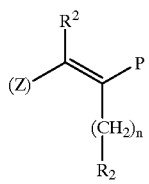

(I)

wherein Z is

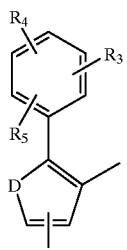 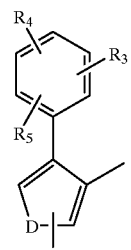 or 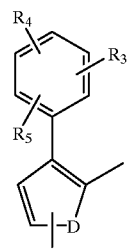

(d)　　(e)　　(f)

D is S;

P is tetrazol-5-yl, $CO_2R_6$ or $C(O)N(R_6)S(O)_qR_{10}$;

$R^a$ is independently hydrogen or $C_{1-6}$alkyl;

$R_1$ is independently hydrogen, Ar, $C_{1-6}$alkyl, or $C_{1-6}$alkoxy;

$R_2$ is Ar, $C_{1-8}$alkyl, $C(O)R_{14}$ or

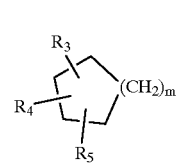

(c)

$R_3$ and $R_5$ are independently hydrogen, $C_2R_6OH$, $R_{13}OH$, $C_{1-8}$alkoxy, $C_{1-8}$alkyl, $S(O)_qR_{11}$, $N(R_6)_2$, $NO_2$, Br, F, I, Cl, $CF_3$, $NHCOR_6$, $R_{13}CO_2R_7$, —X—$R_9$—Y, —X(C($R_6)_2$)$OR_6$, —($CH_2$)$_m$X'$R_8$ or —X($CH_2$)$_n$$R_8$ wherein each methylene group within —X($CH_2$)$_n$$R_8$ may be unsubstituted or substituted by one or two —($CH_2$)$_n$Ar groups;

$R_4$ is independently hydrogen, $R_{11}$, OH, $C_{1-5}$alkoxy, $S(O)_qR_{11}$, wherein $R_{11}$ is $C_{1-5}$alkyl it may be unsubstituted or substituted by OH, methoxy or halogen; $N(R_6)_2$, Br, F, I, Cl or $NHCOR_6$, wherein the $C_{1-5}$alkoxy may be unsubstituted or substituted by OH, methoxy or halogen;

$R_6$ is independently hydrogen or $C_{1-8}$alkyl;

$R_7$ is independently hydrogen, $C_{1-10}$alkyl, $C_{2-10}$alkenyl or $C_{2-8}$alkynyl, all of which may be unsubstituted or substituted by one or more OH, $N(R_6)_2$, $CO_2R_{12}$, halogen or $XC_{1-10}$alkyl; or $R_7$ is $(CH_2)_nAr$;

$R_8$ is independently $R_{11}$, $CO_2R_7$, $CO_2C(R_{11})_2O(CO)XR_7$, $PO_3(R_7)_2$, $SO_2NR_7R_{11}$, $NR_7SO_2R_{11}$, $CONR_7SO_2R_{11}$, $SO_3R_7$, $SO_2R_7$, $P(O)(OR_7)R_7$, CN, $CO_2(CH_2)_mC(O)N(R_6)_2$, $C(R_{11})_2N(R_7)_2$, $C(O)N(R_6)_2$, $NR_7C(O)NR_7SO_2R_{11}$, or $OR_6$, or tetrazole which is substituted or unsubstituted by $C_{1-6}$alkyl;

$R_9$ is independently a bond, $C_{1-10}$alkylene, $C_{1-10}$alkenylene, $C_{1-10}$alkylidene, $C_{1-10}$alkynylene, all of which may be linear or branched, or phenylene, all of which may be unsubstituted or substituted by one of more OH, $N(R_6)_2$, COOH or halogen;

$R_{10}$ is independently $C_{1-10}$alkyl, $N(R_6)_2$ or Ar;

$R_{11}$ is independently hydrogen, Ar, $C_{1-8}$alkyl, $C_{2-8}$alkenyl, $C_{2-8}$alkynyl, all of which may be unsubstituted or substituted by one or more OH, $CH_2OH$, $N(R_6)_2$ or halogen;

$R_{12}$ is independently hydrogen, $C_{1-6}$alkyl, $C_{2-6}$alkenyl or $C_{2-7}$alkynyl;

$R_{13}$ is independently divalent Ar, $C_{1-10}$alkylene, $C_{1-10}$alkylidene, $C_{2-10}$alkenylene, all of which may be unsubstituted or substituted by one or two $CO_2R_6$, OH, $CH_2OH$, $N(R_6)_2$ or halogen;

$R_{14}$ is independently hydrogen, $C_{1-10}$alkyl, $XC_{1-10}$alkyl, Ar or XAr;

$R_{15}$ is independently $C_{1-6}$alkyl, cyclopropylmethyl, cyclopropylethyl or phenyl substituted by one or two C1–6alkyl, OH, C1–5alkoxy, $S(O)_qR6$, $N(R6)2$, Br, F, I, Cl, CF3 or $NHCOR_6$;

X is independently $(CH_2)_n$, O, $NR_6$ or $S(O)_q$;

X' is independently O, $NR_6$ or $S(O)_q$;

Y is independently $CH_3$ or $X(CH_2)_nAr$;

Ar is:

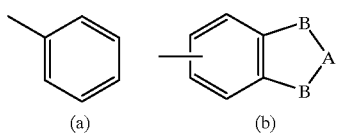

(a)     (b)

naphthyl, indolyl, pyridyl, thienyl, oxazolidinyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or two $Z_1$ or $Z_2$ groups;

A is independently C=O, or $(C(R_6)_2)_m$;

B is independently —$CH_2$— or —O—;

$Z_1$ and $Z_2$ are independently hydrogen, $XR_6$, $C_{1-8}$alkyl, $C_{1-6}$alkoxy, $(CH_2)_qCO_2R_6$, $C(O)N(R_6)_2$, CN, $(CH_2)_nOH$, $NO_2$, F, Cl, Br, I, $N(R_6)_2$, $NHC(O)R_6$, $O(CH_2)_mC(O)NR_aSO_2R_{15}$, $(CH_2)_mOC(O)NR_aSO_2R_{15}$, or $O(CH_2)_mNR_aC(O)NR_aSO_2R_{15}$ or tetrazolyl which may be substituted or unsubstituted by $C_{1-6}$alkyl, $CF_3$ or $C(O)R_6$;

m is independently 1 to 3;

n is independently 0 to 6;

q is independently 0, 1 or 2;

provided $R_3$, $R_4$ and $R_5$ are not O—$O(CH_2)_n$Ar or O—$OR_6$;

or a pharmaceutically acceptable salt thereof.

2. A compound of claim 1 wherein P is $CO_2R_6$; $R_1$ is hydrogen; $R_2$ is Ar, cyclohexyl or $C_{1-4}$alkyl; $R_3$ and $R_5$ are independently hydrogen, $CO_2R_6$, OH, $C_{1-8}$alkoxy, $C_{1-8}$alkyl, $N(R_6)_2$, $NO_2$, Br, F, Cl, I, $R_{13}CO_2R_7$, $X(CH_2)_nR_8$, $(CH_2)_mX'R_8$, or $X(C(R_6)_2)_mOR_6$; $R_4$ is hydrogen, OH, $C_{1-5}$alkoxy, $N(R_6)_2$, Br, F, Cl, I, $NHCOCH_3$, or $S(O)_q$ $C_{1-5}$alkyl wherein the $C_{1-5}$alkyl may be unsubstituted or substituted by OH, methoxy or halogen; $R_6$ is hydrogen, methyl or ethyl; $R_7$ is hydrogen, $C_{1-10}$alkyl, $C_{2-10}$alkenyl or $C_{2-8}$alkynyl, all of which may be unsubstituted or substituted by one or more OH, $N(R_6)_2$, $CO_2R_{12}$, halogen, or $R_7$ is $(CH_2)_n$Ar wherein n is zero or 1 and Ar is substituted phenyl; $R_{11}$ is hydrogen, phenyl, pyridyl allof which may be substituted or unsubstituted by one or two $C_{1-4}$alkyl groups; $C_{1-8}$alkyl, $C_{2-8}$alkenyl, or $C_{2-8}$alkynyl, all of which may be substituted or unsubstituted by one or more OH, $CH_2OH$, $N(R_6)_2$, or halogen; $R_{12}$ is hydrogen or $C_{1-6}$alkyl; $R_{13}$ is phenyl, pyridyl, or $C_{2-10}$alkylene, all of which may be unsubstituted or substituted by one or more $CO_2R_6$, OH, $CH_2OH$, $N(R_6)_2$, or halogen; and $R_{15}$ is hydrogen or $C_{1-6}$alkyl.

3. A compound of claim 2 wherein P is $CO_2H$; $R_1$ is hydrogen; $R_2$ is a group Ar wherein Ar is a group (a) or (b) and in said group (a) or (b), $Z_1$ and $Z_2$ are independently hydrogen, $CO_2R_6$, $(CH_2)_nOH$, $C_{1-4}$alkyl or $C_{1-6}$alkoxy and A is $CH_2$, and one or both Bs are O; $R_3$ is Br, Cl, $C_{1-8}$alkoxy or $X(CH_2)_nR_8$, wherein X is O, n is 0, 1, or 2, and $R_8$ is selected from: $CO_2H$, OH, tetrazolyl optionally substituted by $C_{1-8}$alkyl; $CONR_7SO_2R_{11}$ wherein $R_7$ is H or $C_{1-8}$alkyl, $R_{11}$ is $C_{1-8}$alkyl or phenyl optionally substituted by Br, Cl, F, $C_{1-8}$alkyl; or $R_8$ is phenyl or pyridyl substituted by one or more Br, Cl, $CO_2H$, $CH_2OH$; $R_5$ is methoxy or $N(R_6)_2$ wherein $R_6$ is H or methyl; $R_4$ is hydrogen; $R_6$ is hydrogen, methyl or ethyl; $R_7$ is hydrogen, $C_{1-10}$alkyl, $C_{2-10}$alkenyl or $C_{2-8}$alkynyl, all of which may be unsubstituted or substituted by one or more OH, $N(R_6)_2$, $CO_2R_{12}$, halogen, or $R_7$ is $(CH_2)_n$Ar wherein $R_7$ is $(CH_2)_n$Ar and n is zero or 1 and Ar is phenyl substituted or unsubstituted by halogen or $C_{1-5}$alkoxy; $R_{11}$ is hydrogen, phenyl, pyridyl wherein the phenyl or pyridyl be substituted or unsubstituted by one or two $C_{1-4}$alkyl groups; $C_{1-8}$alkyl, $C_{2-8}$alkenyl, $C_{2-8}$alkynyl, all of which may be substituted or unsubstituted by one or more OH, $CH_2OH$, $N(R_6)_2$, or halogen; $R_{12}$ is hydrogen or $C_{1-6}$alkyl; $R_{13}$ is phenyl, pyridyl, or $C_{2-10}$alkylene, all of which may be unsubstituted or substituted by one or more $CO_2R_6$, OH, $CH_2OH$, $N(R_6)_2$, or halogen; and $R_{15}$ is hydrogen, ethyl, isopropyl, n-butyl, cyclopropylmethyl or cyclopropylethyl.

4. A compound of claim 1 selected from:

E-3-[3-[2-(2-carboxyphenyl)methoxy-4-methoxy] phenyl-thien-2-yl]-2-[2-methoxy-4,5-methylenedioxy ]methyl-prop-2-enoic acidc.

5. A pharmaceutical composition comprising a compound of claim 1 and a pharmaceutically acceptable carrier.

6. A method of treatment of diseases caused by an excess of endothelin comprising administering to a subject in need thereof, an effective amount of an endothelin receptor antagonist of claim 1.

7. A method of treating renal failure or cerebrovascular disease which comprises administering to a subject in need thereof, an effective amount of a compound of claim 1.

8. A method for the prophylaxis and treatment of radio-contrast induced renal failure which comprises administering to a subject in need thereof, an effective amount of a compound of claim 1.

9. A method of treatment of congestive heart failure which comprises administering to a subject in need thereof, an effective amount of a compound of claim 1.

10. A method of treatment of unstable angina, coronary vasospasm and myocardial salvage which comprises administering to a subject in need thereof, an effective amount of a compound of claim 1.

11. A method of preventing or treating restenosis which comprises administering to a subject in need thereof, an effective amount of a compound of claim 1.

12. A method of treatment of pulmonary hypertension which comprises administering to a subject in need thereof, an effective amount of a compound of claim 1.

13. A method of treatment of stroke or subarachnoid hemorrhage which comprises administering to a subject in need thereof, an effective amount of a compound of claim 1.

14. A process for preparing a compound of Formula (I) of claim 1 by:

(a) Reaction of a compound of Formula (II)

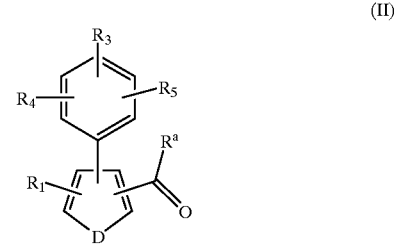

or a protected form or precursor thereof with a compound of Formula (7)

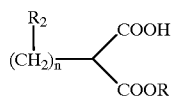

(7)

(wherein $R_2$ is defined for Formula (I) hereinabove); followed if necessary or desired by:

(b) conversion of one compound of Formula (I) into a different compound of Formula (I)
  (i) when Formula (I) contains a group $CO_2R_6$, $CO_2R_7$ or $CO_2R_{12}$ wherein $R_6$, $R_7$ or $R_{12}$ is alkyl, conversion to a corresponding compound where $R_6$, $R_7$ or $R_{12}$ represents hydrogen;
  (ii) when Formula (I) contains a hydroxy group conversion to a different group, and/or (c) salt formation.

* * * * *

UNITED STATES PATENT AND TRADEMARK OFFICE
CERTIFICATE OF CORRECTION

PATENT NO : 6,051,599

DATED : April 18, 2000

INVENTOR(S) : Elliott, et al.

It is certified that errors appear in the above-identified patent and that said Letters Patent is hereby corrected as shown below:

On the title page, item [62]:
  Continuing Data As Claimed By Applicant –
  This is a divisional of application Serial No. 08/737,851, filed February 2, 1998; which is a 371 of International Application No. PCT/US96/12583, filed August 2, 1996; which claims the benefit of the following provisional applications: 60/001,783, filed August 2, 1995 and 60/010,983, filed February 1, 1996.

Item [75]:
  Inventors: John Duncan Elliott, Wayne; Aiming Gao, Chester Springs, and Jia-Ning Xiang, Wayne, all of Pa.

Signed and Sealed this

Sixth Day of March, 2001

Attest:

NICHOLAS P. GODICI

Attesting Officer

Acting Director of the United States Patent and Trademark Office